United States Patent [19]
Wallshein

[11] 4,086,702
[45] May 2, 1978

[54] MULTI-STRANDED COILED ORTHODONTIC ARCH WIRE

[76] Inventor: Melvin Wallshein, 8645 Bay Pkwy., Brooklyn, N.Y. 11214

[21] Appl. No.: 708,304

[22] Filed: Jul. 26, 1976

[51] Int. Cl.² .............................................. A61C 7/00
[52] U.S. Cl. .................................................... 32/14 A
[58] Field of Search ............................. 32/14 A, 14 E

[56] References Cited

U.S. PATENT DOCUMENTS

| 3,729,824 | 5/1973 | Baues et al. | 32/14 A |
| 3,838,515 | 10/1974 | Paugh et al. | 32/14 A |

OTHER PUBLICATIONS

American Journal of Orthodontics, vol. 49 No. 12, Dec. 1963, p. 8 "Unitek, HI-T Coil Springs".

*Primary Examiner*—Robert Peshock
*Attorney, Agent, or Firm*—Flynn & Frishauf

[57] ABSTRACT

An orthodontic arch wire adapted to be received within the channel of an orthodontic bracket includes a plurality of flexible metallic strands wound into a tightly wound elongated coil normally having an array of successively abutting and generally parallel turns. The coiled wire is made from a material sufficiently flexible to permit bending of the arch wire by selectively and at least partially separating adjacent turns thereof. According to a preferred embodiment, the wires are wound interleaved with one another so that adjacent turns are formed by different strands. A plurality of wires may be associated together to from a composite strand, and this composite strand may be used to form the elongated coil.

51 Claims, 23 Drawing Figures

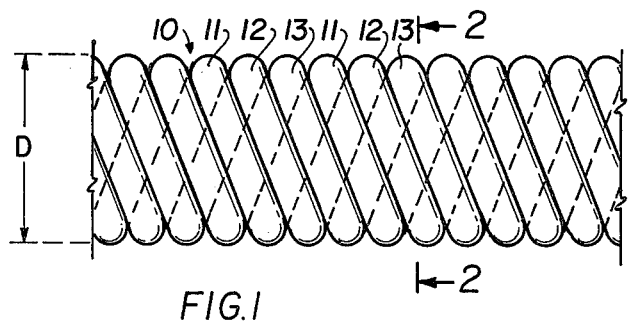
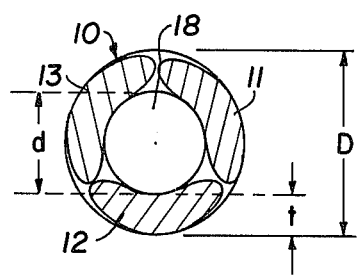
FIG.1    FIG.2
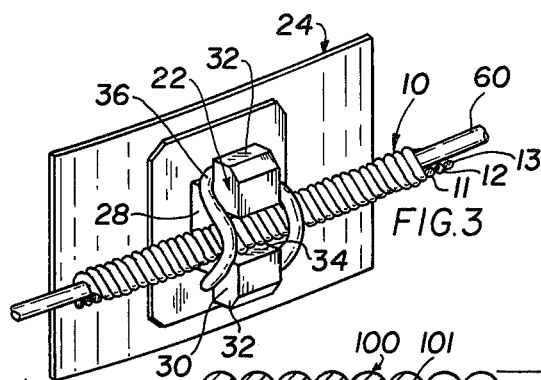
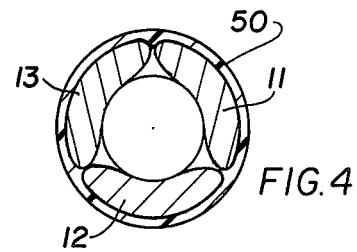
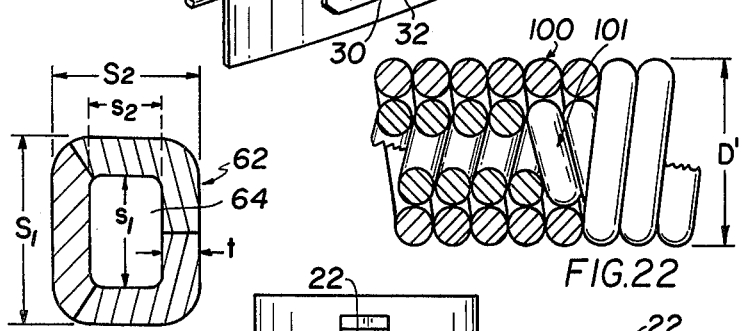
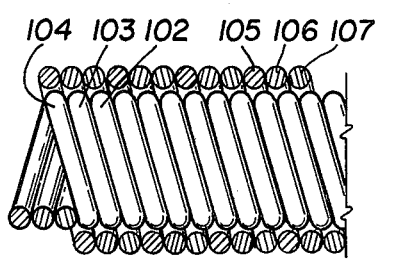
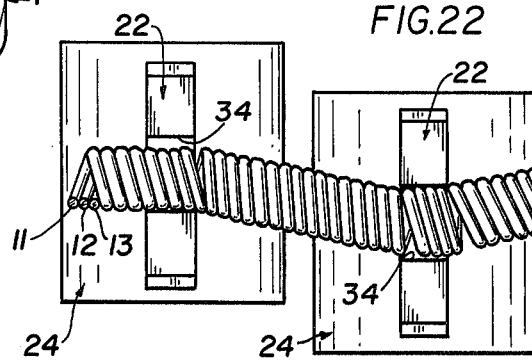
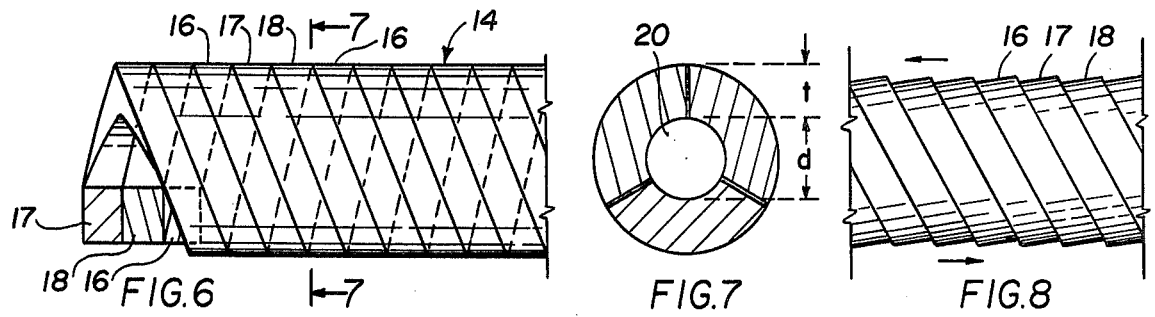
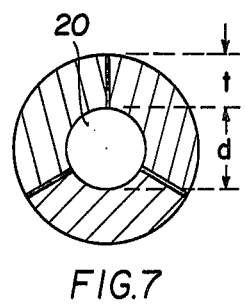
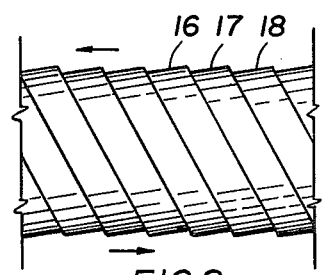

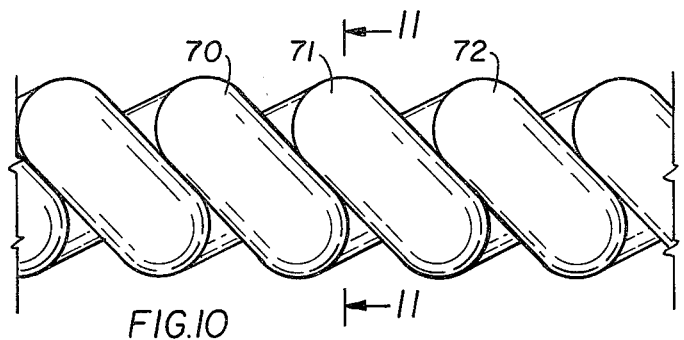
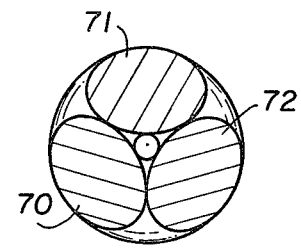
FIG.10  FIG.11
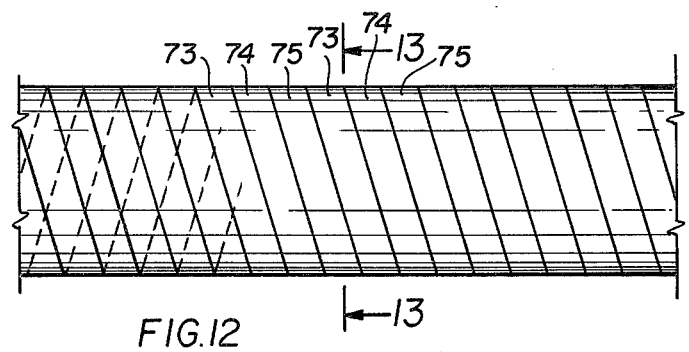
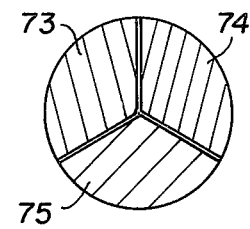
FIG.12  FIG.13
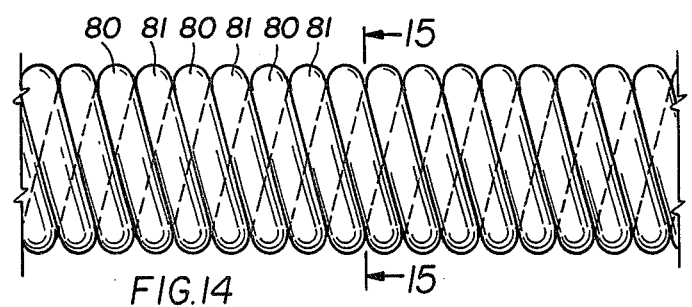
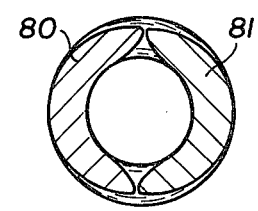
FIG.14  FIG.15
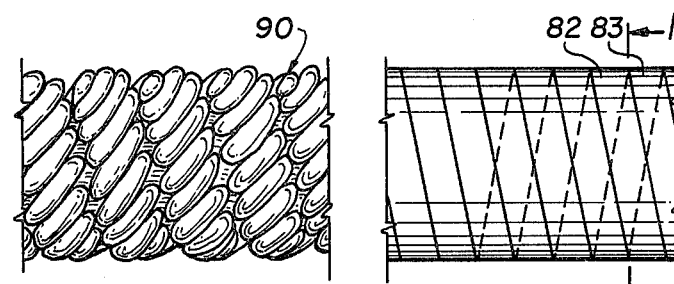
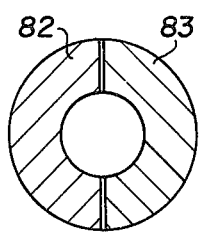
FIG.21  FIG.16  FIG.17
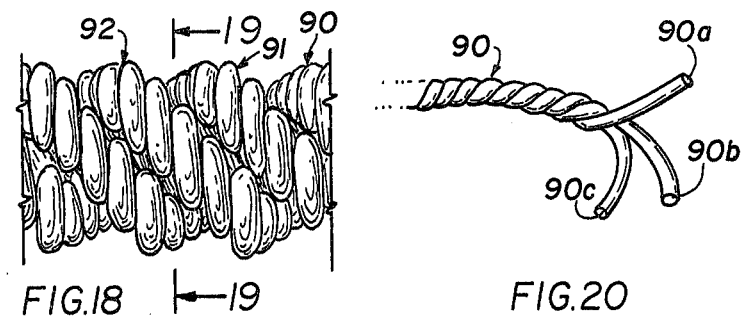
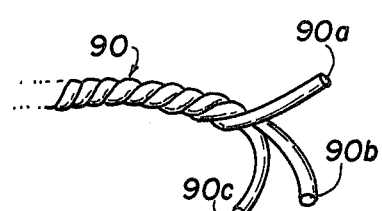
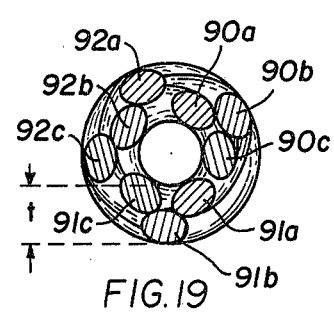
FIG.18  FIG.20  FIG.19

MULTI-STRANDED COILED ORTHODONTIC ARCH WIRE

BACKGROUND OF THE INVENTION

The present invention generally relates to orthodontic arch wires, and more particularly to an arch wire formed of a plurality of metallic strands in the form of a tightly wound elongated coil.

The following definitions apply to the specification and claims. "Stiffness" is the resistance of a material to bending or deformation. "Flexibility" is the ability of a material to bend or deform. "Plastic deformation" is a permanent change in the shape of a material. Once plastic deformation takes place, the removal of forces which caused the change in shape does not result in a return of the material to its original shape. The "elastic limit" of a material is the maximum load or deformation which can be applied to a material before plastic or permanent deformation takes place. "Resiliency" is the tendency of a flexed material to spring back to its original configuration on the removal of the flexing forces. "Working Range" is the range of deformation of a material where it retains its resiliency, up to a maximum deformation which can be sustained by a material without exceeding the elastic limit and becoming permanently deformed with loss of resiliency.

Orthodontic procedures usually require the placement of a tooth band and bracket upon respective maloccluded teeth and the employment of an arch wire for interconnecting the bands or brackets relative to one another so that a force is transmitted from one band to the next and thereby to the teeth upon which the bands are mounted. Today, the orthodontist is offered a wide variety of arch wires. The known arch wires vary both in size and material. An ideal arch wire must be flexible, but must have sufficient stiffness or body over long lengths so that it can serve as a relatively fixed anchoring or reference point to which other orthodontic devices can be connected. The flexibility, of course, is required so that the arch wire can be bent into the shape of an arch in the mouth. It is also desirable that the arch wire have a resiliency and sufficient range over short and long lengths in order to permit the application of local biasing forces to the teeth.

Coiled arch wires consisting of a single metallic strand in the form of a tightly wound helix are known from my earlier U.S. Pat. Nos. 3,861,042, issued Jan. 21, 1975 and 3,878,609, issued Apr. 22, 1975. Coiled orthodontic arch wires made of a single coiled strand are also disclosed in my copending U.S. Application Ser. No. 535,687, filed Dec. 3, 1974.

The object of the present invention is to provide an orthodontic arch wire fabricated of a plurality of strands which are wound in the form of an elongated coiled arch wire, and which would have generally similar if not better characteristics than my earlier coiled arch wires which are formed of a single tightly wound strand.

SUMMARY OF THE INVENTION

According to the present invention, an orthodontic arch wire, which is adapted to be received within a guide channel of an orthodontic bracket mounted on a tooth, comprises a plurality of metallic strands wound into a tightly wound elongated coil and normally having an array of successively abutting and generally parallel turns. The turns may be circular, rectangular, or any other desired shape, and the turns together define a coil having an elongated lumen therethrough. The strands, when formed into said turns, each have a predetermined radial thickness. The turns also have a common internal radial dimension no greater than three times the predetermined radial thickness of the strand. The elongated coil has a common outer diameter or dimension no greater than approximately 0.025 inch and, in the case of a rectangular coil, the outer dimensions are no greater than approximately 0.025 inch by 0.032 inch. These dimensions correspond to those dimensions of the guide channel of an orthodontic bracket into which the arch wire is to be received. The elongated coil is made from a material sufficiently elastic to permit bending of the arch wire over a short length thereof by selectively and at least partially separating adjacent turns, and to provide sufficient stiffness over an elongated length thereof to provide suitable characteristics for orthodontic devices attached thereto.

In a further preferred embodiment of the present invention, the turns have a common internal radial dimension no greater than twice the predetermined radial thickness of the strand. In certain orthodontic applications, a strand having these physical dimensions has characteristics which may be preferable.

According to a further feature of the invention, a mandrel extends through the elongated lumen of the wire. According to a still further feature of the invention, a resilient coating made from an elastomeric material is provided on the exterior portion of the coiled wire for enclosing same. The strands from which the coiled wire are formed may have circular or rectangular cross-sections, and may be either identical or different in metallic construction.

BRIEF DESCRIPTION OF THE DRAWINGS

FIG. 1 is a front view of a cylindrical orthodontic arch wire in accordance with one embodiment of the present invention;

FIG. 2 is a cross-sectional view taken along the line 2 — 2 in FIG. 1;

FIG. 3 is an enlarged perspective view of an orthodontic arch wire similar to that of FIG. 1, but with a mandrel therein, mounted on an orthodontic bracket;

FIG. 4 is a view similar to that of FIG. 2, showing an elastomeric coating on the exterior of the arch wire;

FIG. 5 is an enlarged front elevational view of adjacent orthodontic brackets as mounted on teeth (not shown) and, as associated with a common orthodontic arch wire pursuant to the embodiment illustrated in FIG. 1;

FIG. 6 is a view, similar to that of FIG. 1, of an alternate embodiment of the present invention which uses a plurality of strands each having a rectangular cross-section;

FIG. 7 is a cross-sectional view taken along the line 7 — 7 in FIG. 6;

FIG. 8 is a view, similar to that of FIG. 6, showing an orthodontic wire according to yet another embodiment of the present invention wherein the turns of the coil are inclined at a steeper angle with respect to the axis of the wire;

FIG. 9 is a cross-sectional view, similar to that of FIG. 7, of a further embodiment of the present invention wherein the arch wire is rectangular and has a rectangular lumen extending therethrough;

FIGS. 10 and 11 illustrate a modified arch wire fabricated in accordance with the present invention;

FIGS. 12 and 13 illustrate an arch wire similar to that of FIGS. 10 and 11, but using rectangular cross-section strands;

FIGS. 14 and 15 illustrate an embodiment similar to that of FIGS. 1–3, but using two strands;

FIGS. 16 and 17 illustrate an embodiment similar to FIGS. 14 and 15, but using rectangular wire;

FIGS. 18–21 illustrate embodiments using a multi-stranded composite strand to fabricate coiled arch wires; and FIGS. 22 and 23 illustrate further embodiments of the invention.

DETAILED DESCRIPTION OF THE PREFERRED EMBODIMENTS

FIGS. 1 – 3 illustrate a first embodiment of the present invention which is generally round and forms a generally cylindrical orthodontic arch wire designated by the reference numeral 10. The arch wire 10 is elongate and defines an axis of symmetry which passes through the central region of the resulting coiled wire. The arch wire of FIGS. 1 and 2 is fabricated from three separate strands, 11, 12, 13, lying adjacent each other and wound in an interleaved manner to form the resultant tightly coiled structure of FIG. 1. Each of the strands of the wire of FIG. 1 has a circular cross-section having a diameter $t$ as shown in FIG. 2. The three strands are tightly wound and have successively abutting looped turns, each turn having a generally circular cross-section. Each turn of the coil defines a plane which is generally parallel to the other respective planes defined by the other turns when the arch wire 10 extends along a straight line. The individual strands are interleaved with one another, each forming an elongated interleaved helical coil structure which has improved characteristics as described in greater detail hereinbelow.

The internal diameter $d$ of the resultant arch wire 10 (see FIG. 2) is equal to or less than three times the diameter or radial thickness $t$ of the individual strands from which the orthodontic arch wire 10 is made. A still further preferred range is to have the internal diameter $d$ equal to or less than twice the diameter or radial thickness $t$ of the individual strands. The outer dimension $D$ of the arch wire 10, to be more fully described hereafter, is in the range of dimensions commonly used for arch wires. The metallic strands from which the arch wire is made are preferably stainless steel, which is relatively flexible in nature and which provides an advantageous arch wire when coiled as shown in the drawings.

The central openings defined by the turns each have an internal dimension $d$ and together form a passage or lumen 18 through the arch wire 10. The passage or lumen 18 is normally created during the formation of the coiled wire — that is, during the winding of the coils. One way of manufacturing the wire in accordance with the present invention comprises winding a plurality of wires into a tightly wound helix about a mandrel 60, shown in FIG. 3, which may or may not be left in the arch wire subsequent to the manufacture thereof. When the mandrel 60 is left in the arch wire 10, different characteristics are obtained which may be desirable in certain instances to apply various orthodontic forces. FIG. 3 illustrates the use of the wire in a bracket with the mandrel 60 left in the arch wire 10. The mandrel 60 may be formed of, for example, twisted wires of any desired number of strands (i.e., FIG. 20) or may be a coiled wire of any number of strands (i.e., FIG. 10, FIG. 22).

Because of the tight abutting relationship of each of the turns of the coil relative to each other, the resultant arch wire 10 is provided with a great degree of stiffness — a degree of stiffness which is greater than that of an openly wound helix made from a similar strand or strands of wire, but less than that of a solid wire of equivalent cross-sectional area. Over long lengths the arch wire 10 is somewhat more flexible and less stiff than its solid wire counterpart. Stiffness is further improved by minimizing the diameter of the internal passage of lumen 18 of the arch wire 10. Selecting the lumen or passage diameter to be a dimension no greater than three times the radial dimension of the strands from which the wire is made has been found to provide satisfactory results. In many instances, however, selecting the lumen or passage diameter to be a dimension not greater than twice the radial dimension of the strands has been found to be still more suitable. The arch wire 10 of the present invention may also sustain large compressive forces in directions longitudinal of the axis of the arch wire without deformation of the arch wire. This is a highly desirable characteristic.

The present invention, which utilizes a plurality of strands of wire wound so as to form interleaved turns of an elongated coiled arch wire has an advantage over my prior arch wires disclosed in U.S. Pat. Nos. 3,861,042 and 3,878,609, and in U.S. Application Ser. No. 535,687, filed Dec. 23, 1974, in that when winding the coil, each of the individual strands is subjected to less elastic deformation than in my prior wires wherein only a single elongated strand was wound in a coil. By virtue of the fact that less elastic deformation is imparted to the individual strands during winding of the coiled arch wire 10 of the present invention, the resulting arch wire will tend to have a greater springiness especially in the longitudinal direction, and will be resiliently yieldable so as to tolerate a higher degree of bending in a direction perpendicular to the longitudinal axis without being subjected to breakage or other damage. This is because the individual wires are "worked" less during formation of the coiled arch wire than in my earlier arrangement. By virtue of the turns being tightly wound and being abutting against each other, stiffness of the wire is generally similar to the wire fabricated in accordance with my prior techniques from a single strand.

FIG. 4 illustrates an embodiment wherein a soft coating 50 may be placed about the exterior of the arch wire 10. The coating 50 can be made from an elastomeric material which can simultaneously serve to protect the tissues in the mouth from the wire as well as to prevent food particles from entering into the spaces in the wire where they may decay and present problems to the patient. The coating 50 when made from an elastic material does not substantially alter the characteristics of the arch wire 10.

As mentioned above, FIG. 3 illustrates a typical arch wire according to the present invention mounted on a bracket 22 which in turn is mounted on a band 24, which in turn is mounted to a tooth (not shown). The bracket 22 has a base portion 28 and a flanged portion 30. The flanged portion 30 is provided with a pair of oppositely directed lips or wings 32 which overlie, in spaced relationship, the base portion 28. The bracket 23 further includes a centrally disposed generally U-shaped wire guide-channel 34. An orthodontic arch wire 10 is receivable in the guide-channel 34. A conventional ligature or fastener 36 is mounted over the oppositely directed lips 32 in a conventional manner so as to be detachably associated with the flanged portion 30 to tightly secure the orthodontic arch wire 10 within the guide-channel 34.

The guide-channel 34 assumes slightly different dimensions depending on the manufacturer and the manufacturing tolerances involved. Typically, with edgewise-type brackets of the type shown and commonly utilized, the U-shaped guide-channel 34 may assume cross-sectional dimensions as large as 0.022 inch by 0.028 inch. Accordingly, the above referred to outer dimension D for a cylindrical or round arch wire may be as large as approximately 0.022 inch while still being receivable within the channel 34 of the edgewise bracket. This is particularly true with oversized channels which are sometimes provided in such brackets. While the present invention contemplates round arch wires having an outer dimension D no greater than approximately 0.025 inch, it should be clear that manufacturing tolerances in such arch wires and the mechanical procedures utilized in the manufacture of these wires may result in variances from the above-mentioned anticipated maximum dimension by as much as several thousandths of an inch. In each case, clearly the outer dimension D of the arch wire is advantageously selected to correspond to the dimensions of the arch wire receiving channel 34 and can, accordingly, have a smaller dimension than the above maximum. The precise outer dimension D of the wire is not in itself critical as long as it is dimensioned to be received within a guide-channel of a bracket as described.

The wire of the present invention is also intended to be utilized with various types of orthodontic brackets, other than the edgewise bracket shown in FIG. 3. For example, the wire 10 may be utilized in conjunction with a Begg-type bracket. The latter brackets typically have wire receiving channels having cross-sectional dimensions of up to 0.022 inch by 0.040 inch. Accordingly, insofar as the round or cylindrical arch wire 10 is concerned, the maximum outer dimension D of 0.025 inch still applies to oversized channels provided in such brackets.

Normally, a plurality of orthodontic brackets are mounted on respective teeth and, thereafter, are interconnected to one another through the intermediary of an orthodontic arch wire 10 in a manner generally exemplified in FIG. 5. In FIG. 5, however, there is omitted from the illustration the fastener 36 illustrated in FIG. 3. The reason for omitting the fastener from FIG. 5 is to permit illustration of the manner by which the orthodontic arch wire 10 pursuant to the first described embodiment illustrated in FIGS. 1 and 2 permits "localized" control over the directional movement of a maloccluded tooth. When the arch wire 10 is appropriately mounted and constrained within the guide channel 34 of each of the orthodontic brackets 22, the arch wire may be longitudinally tightened so as to cause movement of the maloccluded teeth in directions generally longitudinally of the wire 10. The arch wire 10 pursuant to the present invention, when mounted within the appropriate guide-channels 34 of each of the orthodontic brackets 22 respectively, may be flexed or bent slightly or significantly. At such time, the turns originally abutting against one another prior to being mounted within the orthodontic brackets 22 will resiliently flex at "localized" positions on either side of the guide-channel 34 of each of the brackets 22. Although slight bending is shown in FIG. 5, the wire 10 can be bent significantly without permanently being deformed and without loss of resiliency. Thus, the wire 10 provides an improved working range over that provided by solid wires. During this process, some of the adjacent turns slightly or at least partially separate from one another in a manner illustrated in FIG. 5. The wire of the present invention has an even greater improved working range over that provided by my earlier single strand coil wires since each of the turns is elastically deformed to a lesser extent in the present invention when the wire is coiled. This permits each of the strands of the coiled wire of the present invention to better retain its resiliency after being wound into the coil and permits the bending of the wire when the turns are separated as illustrated in FIG. 5 over a longer length of wire than in the case of my prior single strand coil wires. This would appear also to provide a longer effective life for the wire according to the present invention.

By providing the tightly wound configuration of the present invention, bending of the arch wire 10 is possible to a greater extent than with prior wires without permanently deforming the resultant wire. The wire of the present invention has excellent flexibility as well as excellent working ranges in small spaces, this being particularly suitable for orthodontic applications. The arch wire according to the present invention has all of the advantages of the wire described in my earlier U.S. Pat. Nos. 3,861,042 and 3,878,609, and in my copending U.S. Pat. Application Ser. No. 535,687.

Although the above embodiment was described in terms of an arch wire or helix of circular cross-section, any other suitable cross-section of the arch wire or configuration of the turns may be utilized. Thus, the turns have been shown to be circular, although rectangular turns, as to be more fully described with reference to FIG. 9, and oval turns may also be utilized. In FIGS. 6 and 7, turns 16, 17 18 are shown which similarly successively abut against each other — the turns being made from interleaved strands of square or rectangular cross-section. As with the first configuration illustrated in FIGS. 1 and 2, the common internal dimension $d$ of the lumen 20 is made equal to or less than three times, and preferably two times, the radial thickness $t$ of the strand from which the orthodontic arch wire 14 is made. As before the orthodontic arch wire 14 is constituted of a plurality of preferably metallic strands such as stainless steel which are flexible in nature and coiled into a square coil with interleaved turns of the wire 14 abutting against adjacent turns. The wire 14 functions generally in the same manner as does the arch wire 10 and exhibits similar properties over long and short lengths as described above. However, by utilizing rectangular strands, the turns define generally smooth external surfaces which do not engage the ligatures 36 and permit the arch wire to axially slide through the channel while captured or maintained therein by the ligatures.

A modified arch wire is shown in FIG. 8 wherein each of the turns defines a plane which is even more oblique to the axis of the respective arch wires. This modification prevents the fastening wires 36 from entering between and separating the adjacent turns since these fastening wires are also generally in planes which are substantially normal to the axis of the arch wires. In FIG. 8, the outer surfaces of the wires form a generally stepped surface. The degree of irregularity of the stepped surface will increase as the pitch angle of the wire increases. While the embodiment of FIG. 6 is shown with a smooth outer periphery, this embodiment will also show a slightly stepped outer surface in practice, but not as severely stepped as the embodiment of FIG. 8.

As suggested above, the arch wire may have a square or rectangular configuration or cross-section instead of the cylindrical cross-section shown, for example, in FIG. 1. The cross-section of such a rectangular wire is shown generally in FIG. 9. The wire is designated by the reference numeral 62 and is formed from strands having a thickness $t$. The wire 62 has common external dimensions designated by S1 and S2. A generally rectangular lumen 64 extends through the arch wire 62 having internal common dimensions s1 and s2. It is pointed out that the wire 62 may be formed from strands having either a circular or rectangular cross-section. When strands or wires having a rectangular cross-section are utilized, the wires are generally wound about one of its longer sides. This is true for both arch wires having rectangular as well as round turns and made from rectangular strands.

As described above, the largest wire receiving channels commonly found in edgewise-type brackets are dimensioned approximately 0.022 inch by 0.028 inch. When a rectangular arch wire 62 is formed, clearly, the outside dimensions thereof S1 and S2 can be made approximately equal to the maximum anticipated dimensions of the arch wire receiving channel. It is anticipated that rectangular arch wires having common outer dimensions no greater than approximately 0.025 inch by 0.032 inch are suitable for most commonly used brackets. This includes the Begg-type brackets whose wire receiving channels may be as large as 0.022 inch by 0.040 inch. Manufacturing techniques and tolerances may result in arch wires having slightly smaller or larger dimensions.

The improved characteristics of the wire can be achieved with the rectangular wire 62 by insuring that the largest common internal dimension s1 is no greater than three times, and in some instances no greater than twice the thickness $t$ of the strand out of which the arch wire is made.

As described above, the use of square or rectangular strands and the formation of either cylindrical or rectangular arch wires is advantageous since it substantially eliminates the notches or curved indentations between adjacent turns, as best shown in FIGS. 1 and 5. This permits substantially free slidable movement of the arch wire through the channel without locking engagement with the ligatures 36.

One method of manufacturing cylindrical arch wires in accordance with the present invention comprises the step of winding a plurality of individual strands, with the strands lying adjacent each other, about a mandrel 60, as shown in FIG. 3. As suggested above, the mandrel may either be left inside the arch wire or removed therefrom prior to use — the characteristics being slightly affected when it is left inside the arch wire and may prove desirable under certain circumstances. However, where most of the work involves longer lengths of arch wire, the mandrel is useful for providing added stiffness and permits the formation of arches as well as loops and U-shapes by deforming the arch wire and the mandrel 60 simultaneously. On the other hand, where most of the work involves bends in small spaces, the mandrel 60 is advantageously removed so as to increase the working range of the arch wire. It should also be noted that loops and U-shapes can similarly be made with this subject arch wire as were made up to now with conventional wires. The rectangular wire can be formed, for example, by compressing a cylindrical wire from opposing sides. A rectangular mandrel may be inserted through the turns prior to compression to assure the formation of a square lumen 64 as shown generally in FIG. 9.

The method according to the present invention can be advantageously used to produce coiled arch wires having a lumen diameter approaching zero or equal to zero. Such an arch wire which comprises three strands 70,71,72 is illustrated, for example, in FIGS. 10 and 11. In accordance with the present invention, the arch wire of FIGS. 10 and 11 is made substantially as described above by winding individual adjacent strands 70,71,72 about a mandrel, such as mandrel 60 shown in FIG. 3. After the wire of FIG. 3 is coiled, the mandrel is removed and the coiled wires are gripped at respective opposite ends and twisted relative to each other to tighten the coil even further and to reduce the lumen diameter to substantially zero. The result of the further twisting operation with the mandrel removed is a wire in which the lumen diameter approaches or is virtually zero or if the further twisting is carried out to the proper degree of tightness, the resulting wire will have a zero lumen diameter. Also, this method can be used to reduce the lumen diameter to any desired size for any of the coiled wires described herein, after the mandrel is removed. This method enables obtaining a tightly twisted wire with a substantially zero lumen diameter more conveniently than has been heretofore possible. As should be apparent, the smaller the lumen, the more rigid the resulting wire will be. Also, as the size of the lumen decreases, the spring action in the longitudinal direction of the elongated coiled wire is reduced. In other words, by substantially eliminating the lumen, lateral flexibility and longitudinal springiness are sacrificed in favor of more rigidity.

While the above method is advantageously carried out when using three adjacent wire strands, it should be clear that the method is applicable to any number of strands, for example 2, 4, etc.

FIGS. 12 and 13 illustrate a wire similar to that of FIGS. 10 and 11, but made with strands 73,74,75, each of which have rectangular cross-sections. The wire of FIGS. 12 and 13 is made similar to the wire of FIGS. 10 and 11 to reduce the lumen to substantially zero diameter. The strands may be deformed to a "sector" shape as seen in FIG. 13 during winding or one may start with strands having "sector-shaped" cross-sections.

FIGS. 14 and 15 illustrate a further embodiment of the present invention, similar to that of FIGS. 1–5, but fabricated from two strands of wire 80,81, each of which having a generally circular cross-section. In the embodiment of FIGS. 14 and 15, the resulting arch wire has an internal lumen which is just less than three times the radial thickness of the strands.

FIGS. 16 and 17 are similar to the embodiment of FIGS. 14 and 15, except the two strand configuration is fabricated from wires having generally rectangular cross-sections. The two strands 82,83 form a generally smooth outer periphery which, in actual practice, is slightly stepped, the slight stepping not being shown in FIG. 16.

According to a further feature of the invention, a plurality of strands of wire may be associated together, for example by twisting, braiding, pressing, or any other suitable manner to form a single composite strand. Such a composite strand 90 is shown in FIG. 20 wherein the composite 90 is formed by twisting individual strands 90a, 90b and 90c. Then, three such composite strands 90,91,92 may be tightly wound into a coil with successively abutting and generally parallel turns, as shown in FIGS. 18 and 19 with a lumen $d$. In the arrangement of FIGS. 18 and 19 the turns of the composite strands have a common internal radial dimension no greater than three times the radial thickness of the composite strand. In a preferred embodiment, the turns have a common internal radial dimension no greater than two times the predetermined radial thickness of the composite strand. The strand of FIGS. 18 and 19 can also be wound and then tightened to provide an arch wire with a substantially zero lumen. The method of reducing the lumen to substantially zero diameter is substantially similar to the method described above with respect to the arch wires of FIGS. 1–13. The wires 90a, 90b, 90c, etc. may have rectangular or other cross-sections. As shown in FIG. 21, a single composite strand 90, formed of a plurality of individual strands, may be wound into a helically wound arch wire with the same restrictions on internal lumen diameter $d$ and thickness $t$ of the composite strand as given above with respect to FIGS. 18 and 19.

FIG. 22 illustrates a further embodiment of the present invention wherein an outer helical coil 100 is wound around an inner helical coil 101, the pitch of the outer coil 100 being opposite to that of the coil 101. In FIG. 22, each of the coils 100,101 is shown comprised of a single strand. However, as shown in FIG. 23, the inner coil may comprise a plurality of adjacent strands, such as shown in FIG. 1, and/or the outer coil may comprise either a single strand as shown in FIG. 22, or one or more strands as shown in FIG. 1. While the arrangement of FIGS. 22 and 23 are illustrated with round wires, the concepts are equally applicable to rectangular wires or any other suitably shaped wire. In FIG. 23, the inner coil is made up of three adjacent wires, 102,103,104 and the outer coil is made up of three adjacent wires 105,106,107. The arrangement of FIG. 23 is exemplary and various combinations of numbers of strands forming the various coils can be used. The resultant composite coils of FIGS. 22 and 23 may be covered with an elastomeric material as illustrated in FIG. 4.

If the coils of FIGS. 22 and 23 are wound in the same direction, the coil diameter of both coils can be simultaneously reduced by twisting opposite ends after a mandrel is removed therefrom.

The outer dimension D′ in FIG. 22 is limited to 0.025 inches so that it may fit within an arch wire channel of a bracket. In a suitable arrangement, the diameters of the wires used in FIG. 22 are all 0.005 and the internal lumen of the inner wire 101 is 0.005 inches or slightly less.

The inner coil in FIGS. 22 and 23 may be formed with or without a lumen, depending upon the desired characteristics of the arch wire. Alternatively, the inner core for the outer coil may be a twisted wire, or example as shown in FIG. 20.

Any of the illustrated coiled wires described above can be rolled into rectangular coils using opposed rollers as described in my copending application Ser. No. 535,687, filed Dec. 23, 1974, or can be impacted or pounded to change their shape from round coils to rectangular.

In preferred arrangements, the orthodontic arch wires, for example the wires of FIGS. 1, 3 and 5, are fabricated from strands having diameters of from, for example, about 0.006 inches to about 0.009 inches. Other diameters may be used, depending upon the nature of the wire and the desired characteristics. In a preferred embodiment using rectangular wire, wires having cross-sectional dimensions of about 0.006 by 0.010 inches have been found to provide good results.

While most of the above embodiments are shown as comprising three individual strands lying adjacent each other and interleaved to form the tightly wound coiled wire, the invention can be carried out with other numbers of strands, for example two strands as illustrated in FIG. 14, four strands, five strands, etc. As the number of strands is reduced, the characteristics of the resulting wire approaches the charactersitics of the wires illustrated in my prior U.S. Pat. Nos. 3,861,042 and 3,878,609 and in my copending Application Ser. No. 535,687.

While the invention has been described above with respect to specific embodiments, numerous alterations of the structure herein disclosed will be apparent to those ordinarily skilled in the art. The illustrated embodiments are only preferred embodiments of the invention which are given for the purpose of illustration only and are not to be construed as a limitation of the invention as set forth in the claims.

I claim:

1. An orthodontic arch wire adapted to be connected to an orthodontic bracket mounted on a maloccluded tooth, the arch wire comprising a plurality of adjacent strands coiled in the form of a tightly wound elongated coiled wire normally having an array of interleaved turns of and generally parallel, and having a lumen extending therethrough, said strands when formed into said turns having a predetermined radial thickness ($t$), said turns having a common internal dimension ($d$-FIG. 2; $s1$-FIG. 9) of said lumen no greater than two times said predetermined radial thickness ($t$) of said strands and having a common outer dimension no greater than approximately 0.025 inches, said strands being made from a material sufficiently elastic to at least permit bending of the arch wire over a short length thereof by selectively and at least partially separating adjacent turns, and to provide sufficient stiffness over a long length to provide adequate anchoring characteristics for orthodontic devices attached thereto.

2. An orthodontic arch wire according to claim 1 wherein said strands each have a generally rectangular cross-section.

3. An orthodontic arch wire according to claim 1 wherein said strands each have a generally circular cross-section.

4. An orthodontic arch wire according to claim 1 wherein said lumen is an elongate axial passage through said turns, and further comprising a resilient mandrel extending through said passage.

5. An orthodontic arch wire according to claim 1 further comprising an external flexible coating extending along and covering the outer surface of said turns.

6. An orthodontic arch wire according to claim 5 wherein said coating is made of an elastomeric material.

7. An orthodontic arch wire according to claim 1 comprising three adjacent strands wound adjacent each other forming said interleaved turns.

8. An orthodontic arch wire according to claim 1 comprising two adjacent strands would adjacent each other forming said interleaved turns.

9. An orthodontic arch wire according to claim 1 wherein said lumen is an elongate axial passage through said turns and is generally circular.

10. An orthodontic arch wire according to claim 1 wherein said lumen is an elongate axial passage through said turns and is generally rectangular.

11. An orthodontic arch wire according to claim 1 wherein each of said adjacent strands comprises a plurality of individual strands associated together to form a composite strand.

12. An orthodontic arch wire according to claim 11 wherein said composite strand comprises a plurality of individual wires twisted together.

13. An orthodontic arch wire adapted to be connected to an orthodontic bracket mounted on a maloccluded tooth, the arch wire comprising a plurality of adjacent strands coiled in the form of a tightly wound elongated coiled wire normally having an array of interleaved turns of said strands, said turns being successively abutting and generally parallel, and having a lumen extending therethrough, said strands when formed into said turns having a predetermined radial thickness ($t$), said turns having a common internal dimension ($d$-FIG. 2; $s1$-FIG. 9) of said lumen greater than two times said predetermined radial thickness ($t$) of said strands and no greater than three times said predetermined radial thickness ($t$) of said strands, and having a common outer dimension no greater than approximately 0.025 inches, said strands being made from a material sufficiently elastic to at least permit bending of the arch wire over a short length thereof by selectively and at least partially separating adjacent turns, and to provide sufficient stiffness over a long length to provide adequate anchoring characteristics for orthodontic devices attached thereto.

14. An orthodontic arch wire according to claim 13 wherein said strands each have a generally rectangular cross-section.

15. An orthodontic arch wire according to claim 13 wherein said strands each have a generally circular cross-section.

16. An orthodontic arch wire according to claim 13 wherein said lumen is an elongate axial passage through said turns, and further comprising a resilient mandrel extending through said passage 17. An orthodontic arch wire according to claim 13 further comprising an external flexible coating extending along and covering the outer surface of said turns.

18. An orthodontic arch wire according to claim 17 wherein said coating is made of an elastomeric material.

19. An orthodontic arch wire according to claim 13 comprising three adjacent strands wound adjacent each other forming said interleaved turns.

20. An orthodontic arch wire according to claim 13 comprising two adjacent strands wound adjacent each other forming said interleaved turns.

21. An orthodontic arch wire according to claim 13 wherein said lumen is an elongate axial passage through said turns and is generally circular.

22. An orthodontic arch wire according to claim 13 wherein said lumen is an elongate axial passage through said turns and is generally rectangular.

23. An orthodontic arch wire according to claim 13 wherein each of said adjacent strands comprises a plurality of individual strands associated together to form a composite strand.

24. An orthodontic arch wire according to claim 23 wherein said composite strand comprises a plurality of individual wires twisted together.

25. An orthodontic arch wire adapted to be connected to an orthodontic bracket mounted on a maloccluded tooth, the arch wire comprising a plurality of wires associated together to form a composite strand, said composite strand being coiled to the form of a tightly wound elongated coil normally having an array of successively abutting and generally parallel adjacent turns, and having a lumen extending therethrough, said composite strand when formed into said turns having a predetermined nominal radial thickness ($t$), said turns having a common internal dimension ($d$-FIG. 2; $s1$-FIG. 9) of said lumen no greater than two times said predetermined radial thickness ($t$) of said composite strand and having a common outer dimension no greater than approximately 0.025 inches, said wires being made from a material sufficiently elastic to at least permit bending of the arch wire over a short length thereof by selectively and at least partially separating adjacent turns, and to provide sufficient stiffness over a long length to provide adequate anchoring characteristics for orthodontic devices attached thereto.

26. An orthodontic arch wire according to claim 25 comprising three of said composite strands located adjacent each other.

27. An orthodontic arch wire according to claim 25 wherein said wires each have a generally circular cross-section.

28. An orthodontic arch wire according to claim 25 wherein said lumen is an elongate axial passage through said turns, and further comprising a resilient mandrel extending through said passage.

29. An orthodontic arch wire according to claim 25 wherein said lumen is an elongate axial passage through said turns and is generally circular.

30. An orthodontic arch wire according to claim 25 wherein said lumen is an elongate axial passage through said turns and is generally rectangular.

31. An orthodontic arch wire according to claim 25 wherein said plurality of wires forming a composite strand are twisted together.

32. An orthodontic arch wire adapted to be connected to an orthodontic bracket mounted on a maloccluded tooth, the arch wire comprising a plurality of wires associated together to form a composite strand, said composite strand being coiled in the form of a tightly wound elongated coil normally having an array of successively abutting and generally parallel adjacent turns, and having a lumen extending therethrough, said composite strand when formed into said turns having a predetermined nominal radial thickness ($t$), said turns having a common internal dimension ($d$-FIG. 2; $s1$-FIG. 9) of said lumen greater than two times said predetermined radial thickness ($t$) of said composite strand and no greater than three times said predetermined radial thickness ($t$) of said composite strand, and having a common outer dimension no greater than approximately 0.025 inches, said wires being made from a material sufficiently elastic to at least permit bending of the arch wire over a short length thereof by selectively and at least partially separating adjacent turns, and to provide sufficient stiffness over a long length to provide adequate anchoring characteristics for orthodontic devices attached thereto.

33. An orthodontic arch wire according to claim 32 comprising three of said composite strands located adjacent each other.

34. An orthodontic arch wire according to claim 32 wherein said wires each have a generally circular cross-section.

35. An orthodontic arch wire according to claim 32 wherein said lumen is an elongate axial passage through said turns, and further comprising a resilient mandrel extending through said passage.

36. An orthodontic arch wire according to claim 32 wherein said lumen is an elongate axial passage through said turns and is generally circular.

37. An orthodontic arch wire according to claim 32 wherein said lumen is an elongate axial passage through said turns and is generally rectangular.

38. An orthodontic arch wire according to claim 32 wherein said plurality of wires forming a composite strand are twisted together.

39. An orthodontic arch wire adapted to be connected to an orthodontic bracket mounted on a maloccluded tooth, the arch wire comprising at least one inner strand coiled in the form of a tightly wound elongated coiled wire normally having an array of successively abutting adjacent turns, and at least one outer strand coiled around said coiled inner strand, said outer coil having a common outer dimension no greater than approximately 0.025 inches, said strands being made from a material sufficiently elastic to at least permit bending of the arch wire over a short length thereof by selectively and at least partially separating adjacent turns, and to provide sufficient stiffness over a long length to provide adequate anchoring characteristics for orthodontic devices attached thereto.

40. An orthodontic arch wire according to claim 39 wherein said at least one outer strand of said outer coil, when formed into said turns, having a predetermined radial thickness ($t$), said outer turns having a common internal dimension ($d$) no greater than three times said predetermined radial thickness ($t$) of said outer strands.

41. An orthodontic arch wire according to claim 39 wherein said at least one outer strand of said outer coil, when formed into said turns, having a predetermined radial thickness ($t$), said outer turns having a common internal dimension ($d$) no greater than two times said predetermined radial thickness ($t$) of said outer strands.

42. An orthodontic arch wire according to claim 39 wherein said outer turn is wound in a direction opposite to the winding direction of said inner coil.

43. An orthodontic arch wire according to claim 39 wherein said inner coil is comprised of a plurality of inner strands wound adjacent each other to form an array of interleaved turns of said strands.

44. An orthodontic arch wire according to claim 43 wherein said outer coil is wound from a plurality of adjacent strands coiled to form an array of interleaved turns of said outer adjacent strands.

45. An orthodontic arch wire according to claim 39 wherein said outer coil is wound from a plurality of adjacent strands coiled to form an array of interleaved turns of said outer adjacent strands.

46. An orthodontic arch wire according to claim 39 wherein said inner turns are wound with a substantially zero lumen.

47. An orthodontic arch wire according to claim 39 wherein said inner turns are wound about a mandrel to form a coil having a predetermined lumen extending therethrough.

48. An orthodontic arch wire according to claim 4 wherein said resilient mandrel comprises a plurality of wires twisted together.

49. An orthodontic arch wire according to claim 16 wherein said resilient mandrel comprises a plurality of wires twisted ogether.

50. An orthodontic arch wire according to claim 28 wherein said resilient mandrel comprises a plurality of wires twisted together.

51. An orthodontic arch wire according to claim 35 wherein said resilient mandrel comprises a plurality of wires twisted together.

* * * * *